(12) United States Patent
Pu

(10) Patent No.: US 6,268,610 B1
(45) Date of Patent: *Jul. 31, 2001

(54) CHARGED-PARTICLE BEAM IRRADIATION APPARATUS, CHARGED-PARTICLE BEAM ROTARY IRRADIATION SYSTEM, AND CHARGED-PARTICLE BEAM IRRADIATION METHOD

(75) Inventor: Yuehu Pu, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/146,036

(22) Filed: Sep. 2, 1998

(30) Foreign Application Priority Data

Oct. 20, 1997 (JP) .................................................. 9-287003

(51) Int. Cl.[7] ........................................................ A61N 5/00
(52) U.S. Cl. ........................................ 250/492.3; 250/398
(58) Field of Search ............................... 250/492.3, 374, 250/492.2, 492.1, 398

(56) References Cited

U.S. PATENT DOCUMENTS

| | | |
|---|---|---|
| 4,367,411 | 1/1983 | Hanley et al. . |
| 4,968,890 * | 11/1990 | Nishihara ........................... 250/374 |
| 5,012,111 * | 4/1991 | Ueda .................................. 250/492.3 |
| 5,039,867 * | 8/1991 | Nishihara et al. ................. 250/492.3 |
| 5,818,058 * | 10/1998 | Nakanishi et al. ................. 250/492.3 |
| 6,034,377 * | 3/2000 | Pu ...................................... 250/492.3 |

OTHER PUBLICATIONS

"The 200–MeV Proton Therapy Project a the Paul Scherrer Institute: Conceptual Design and Practical Realization" by Pedroni et al, Med. Phys. 22(1), Jan. 1995, pp. 37–53.

"Instrumentation for Treatment of Cancer Using Proton and Light–Ion Beams" by Chu et al, Rev. Sci. Instrum. 64 (8), Aug. 1993.

* cited by examiner

Primary Examiner—Teresa M. Arroyo
Assistant Examiner—Johnnie L Smith, II
(74) Attorney, Agent, or Firm—Sughrue, Mion, Zinn, Macpeak & Seas, PLLC

(57) ABSTRACT

A charged-particle beam irradiation apparatus capable of realizing spot-scanning in which the spot of a beam parallel to the axis of incidence thereof is shifted in two axial directions within a radiation area, and having a compact and lightweight design. A pair of scanning electromagnets, that are linked by linkage frames, generate a scanning field composed of a pair of magnetic fields effective in bending a charged-particle beam by the same angle in mutually opposite directions. Rotation of the apparatus is accomplished by rotary driving gear having the scanning electromagnets mounted thereon and motors. Thus, spot scanning in which the spot of a beam parallel to the axis of incidence thereof is shifted in two axial directions can be realized.

11 Claims, 14 Drawing Sheets

DENSITY DISTRIBUTION OF NUMBERS OF DEPOSITED PARTICLES N(X,Y)

CHARGED-PARTICLE BEAM IRRADIATION APPARATUS, CHARGED-PARTICLE BEAM ROTARY IRRADIATION SYSTEM, AND CHARGED-PARTICLE BEAM IRRADIATION METHOD

BACKGROUND OF THE INVENTION

1. Field of the Invention

The present invention relates to a charged-particle beam irradiation apparatus, a charged-particle beam rotary irradiation system, and a charged-particle beam irradiation method which are adapted to a therapeutic apparatus using a charged-particle beam or the like.

2. Description of the Related Art

FIG. 16 shows an example of a charged-particle beam rotary irradiation system that is a conventional therapeutic apparatus using a charged-particle beam disclosed in, for example, a report written by Pedroni of Switzerland (Medical Physics, Vol. 22, PP.37–53).

In the drawing, there are shown a charged-particle beam rotary irradiation system 100, a particle accelerator 1, a transporting electromagnet 3, an energy degrader 5, a proton beam 7, a beam stopper 9, a rotating gantry 10, deflective electromagnets 11, 13, and 19, convergent electromagnets 15, a scanning electromagnet.17, an energy degrader 21, a dose/position monitor 23, a patient 25, a radiation table 27, and an axis of rotation of the gantry 29.

A proton beam generated by the accelerator 1 is transported by the transporting electromagnet 3, passed by the energy degrader 5 serving as an initial-stage energy changing means, and thus recomposed into a proton beam 7 having given energy level. The proton beam 7 is deflected upward from a horizontal direction by the first deflective electromagnet 11, and then returned to the horizontal direction by the deflective electromagnet 13.

The proton beam 7 is converged by the convergent electromagnets 15, and swept vertically by the scanning electromagnet 17. The swept proton beam is deflected immediately downward by the last deflective electromagnet 19, and then irradiated to the patient 25 via the energy degrader for fine adjustment 21 and the dose/position monitor 23.

Herein, the electromagnets 11, 13, 15, 17, and 19, energy degrader 21, and monitor 23 are integrated into one unit, thus forming an irradiation gantry. The irradiation gantry can make a turn about the axis of rotation 29 and is referred to as the rotating gantry 10.

The spot of the proton beam irradiated to the patient 25 is shifted parallel to an X-axis direction alone shown in FIG. 16 by means of the scanning electromagnet 17 and deflective electromagnet 19. Scanning the patient in a Y-axis direction which is required for a therapeutic procedure is achieved by moving the radiation table 27. Scanning the patient 25 in a depth direction (Z-axis direction) of the patient 25 is achieved by adjusting the energy of the proton beam using the energy degrader 21.

The length of the rotating gantry 10 in the longitudinal direction thereof is approximately 10 m. A length in the gantry where the proton beam is displaced away from the gantry rotation axis 29 is approximately 2 m.

In the thus-configured conventional modality using a charged-particle beam, spot scanning in which the spot of a beam is shifted parallel to one axial direction alone (the X-axis direction in the above example) can solely be realized. The patient 25 must be moved in the Y-axis direction by moving the table 27 during treatment. This poses a problem that the movement gives the patient senses of discomfort and fear and results in displacement of a radiation area.

Moreover, in the above conventional modality, since the spot of a beam parallel to an axis of incidence thereof is shifted, the scanning electromagnet 17 must be placed upstream of the deflective electromagnet 19. Accordingly the deflective electromagnet 19 for deflecting a proton beam, i.e. the charged-particle beam, which is swept vertically by the scanning electromagnet 17, becomes large in size. As a result, the total weight of the treatment rotating gantry 10 becomes 100 tons or more. Moreover, since the deflective electromagnet 19 is so large as to have magnetic poles of several tens centimeters wide, when a superconducting magnet is employed, there arises a problem of very high manufacturing cost.

SUMMARY OF THE INVENTION

The present invention attempts to solve the aforesaid problems. An object of the present invention is to provide a charged-particle beam irradiation apparatus, charged-particle beam rotary irradiation system, and charged-particle beam irradiation method realizing spot scanning, in which the spot of a beam parallel to an axis of incidence thereof is shifted two axial directions within a radiation area, without the necessity of moving a table, and employing a rotating gantry of a compact and lightweight design.

For accomplishing the above object, according to the present invention, there is provided a charged-particle beam irradiation apparatus comprising a scanning field generating means for generating a scanning field composed of a pair of fields effective in bending a charged-particle beam by the same angle in mutually opposite directions, and a rotating means for rotating the scanning field generating means with the axis of incidence of the charged-particle beam as a center.

Moreover, according to the present invention, there is provided a charged-particle beam irradiation apparatus characterized in that the scanning field generating means generates magnetic fields.

Moreover, according to the present invention, there is provided a charged-particle beam irradiation apparatus characterized in that the scanning field generating means generates electric fields.

Moreover, according to the present invention, there is provided a charged-particle beam rotary irradiation system comprising: a deflecting means for deflecting a charged-particle beam perpendicularly to a radiation plane; a charged-particle beam irradiation apparatus that includes a scanning field generator, located downstream of the deflecting means, for generating a scanning field composed of a pair of fields effective in bending the charged-particle beam by the same angle in mutually opposite directions, and a rotator for rotating the scanning field generator with the axis of incidence of the charged-particle beam as a center, and that sweeps the charged-particle beam deflected by the deflecting means for the purpose of scan; a charged-particle beam energy adjusting means interposed between the charged-particle beam irradiation apparatus and an irradiated subject; and a rotary motion means for rotating at least the deflecting means and charged-particle beam irradiation apparatus in one united body.

Moreover, according to the present invention, the charged-particle beam falls on the deflecting means from the direction of the axis of rotation of the rotary motion means.

The deflecting means includes three deflective electromagnets for deflecting an incident charged-particle beam three times by 90° with respect to a direction parallel to the radiation plane so that the charged-particle beam is perpendicular to the radiation plane. The irradiated subject is positioned on the axis of rotation of the rotary motion means.

Moreover, according to the present invention, there is provided a charged-particle beam rotary irradiation system characterized in that the deflective electromagnets included in the deflecting means are realized with superconducting electromagnets.

Moreover, according to the present invention, there is provided a charged-particle beam irradiation system comprising: a charged-particle beam irradiation apparatus that includes a scanning field generator for generating a scanning field composed of a pair of fields effective in bending a charged-particle beam by the same angle in mutually opposite directions, and a rotator for rotating the scanning field generator with the axis of incidence of the charged-particle beam as a center, and that sweeps the charged-particle beam for the purpose of scan; a charged-particle beam energy adjusting means, interposed between the charged-particle beam irradiation apparatus and irradiated subject, for adjusting the energy of a charged-particle beam; a dose/position measuring means, interposed between the charged-particle beam irradiation apparatus and irradiated subject, for monitoring the dose and position of an irradiated charged-particle beam; and a control means, connected to the respective means, for controlling scan. The control means includes: a first means for setting the angle of rotation and field intensity concerning the scanning field generator, and the energy of the charged-particle beam according to a group of coordinates [Pi: i=1, 2, . . . , n] (i=1 that is an initial value) defining a radiation area; a second means for irradiating a charged-particle beam according to the setting; a third means for, when the number of deposited particles of the charged-particle beam becomes equal to or larger than a pre-set number of particles or when a coordinate of a position to which a charged-particle beam is irradiated is inconsistent with a coordinate of a pre-set position, stopping the charged-particle beam; and a fourth means that when a charged-particle beam is stopped, judges whether or not irradiation to the whole radiation area is completed, that if the irradiation is not completed, increments i by one, modifies the angle of rotation and field intensity concerning the scanning field generator, and the energy of the charged-particle beam in a given order, and thus actuates the first to third means repeatedly, and that if the irradiation is completed, terminates irradiation.

According to the present invention, the fourth means retains the angle of rotation of the scanning field generator at a certain value, modifies the intensity of a field generated by the scanning field generator and the energy of a charged-particle beam in given order, and thus actuates the first to third means repeatedly.

According to the present invention, there is provided a charged-particle beam irradiation system comprising: a charged-particle beam irradiation apparatus that includes a scanning field generator for generating a scanning field composed of a pair of fields effective in bending a charged-particle beam by the same angle in mutually opposite directions, and a rotator for rotating the scanning field generator with the axis of incidence of the charged-particle beam as a center, and that sweeps the charged-particle beam for the purpose of scan; a charged-particle beam energy adjusting means, interposed between the charged-particle beam irradiation apparatus and an irradiated subject, for adjusting the energy of a charged-particle beam; a dose/position measuring means, interposed between the charged-particle beam irradiation apparatus and irradiated subject, for monitoring the does and position of an irradiated charged-particle beam; a means for stopping a charged-particle beam; and a control means, connected to the respective means, for controlling scan. The control means includes: a first means for setting the energy of a charged-particle beam to be irradiated according to a coordinate of a position indicating a depth to which a beam is irradiated, $Z_i$ (i=1 that is an initial value), specified in a group of coordinates [($Z_i$, $\theta_{ij}$), i=1, 2, . . . , m, j=1, 2, . . . , n] defining a radiation area; a second means for specifying the angle of rotation of the scanning field generator in $\theta_{ij}$ (j=1 that is an initial value) and specifying a set defining a scan pattern that is a characteristic curve relative to time in $I_{ij}(t)$; a third means for irradiating a charged-particle beam according to the setting and specification, driving the scanning field generator according to the scan pattern that is the characteristic curve relative to time defined by $I_{ij}(t)$, and thus sweeping the charged-particle beam so as to achieve a given number of scans; a fourth means for judging in parallel with the scans achieved by the third means whether or not a coordinate of a position to which a charged-particle beam is irradiated is consistent with a coordinate of a pre-set position; a fifth means for, when the given number of scans have been carried out or when the coordinate of the position at which a charged-particle beam is irradiated is inconsistent with the coordinate of the pre-set position, stopping the charged-particle beam; and a sixth means that when a charged-particle beam is stopped, judges whether or not irradiation to the whole radiation area is completed, that if the irradiation is completed, terminates irradiation, that if the irradiation is not completed, judges whether or not the coordinate of the position indicating a depth to which a beam is irradiated, $Z_i$, should be changed to the next value, that if the coordinate is not changed, increments j by one and actuates the second to fifth means repeatedly, and that if the coordinate is changed, increments i by one, resets j to the initial value of 1, and actuates the first to fifth means repeatedly.

According to the present invention, there is provided a charged-particle beam irradiation system characterized in that $I_{ij}(t) \sqrt{t}$ is adopted as $I_{ij}(t)$ defining the scan pattern that is the characteristic curve relative to time to be followed by the scanning field generator.

According to the present invention, there is provided a charged-particle beam irradiation method, in which a scanning field generating means for generating a scanning field composed of a pair of fields effective in bending a charged-particle beam by the same angle in mutually opposite directions is used to shift the spot of a charged-particle beam along one straight line on a plane perpendicular to the axis of incidence of the charged-particle beam, and rotated with the axis of incidence as a center in order to irradiate the charged-particle beam to a radiation area, comprising: a first step of setting the angle of rotation and field intensity concerning the scanning field generating means, and the energy of a charged-particle beam according to a group of coordinates [Pi: i=1, 2, . . . n] (i=1 that is an initial value) defining the radiation field; a second step of irradiating a charged-particle beam according to the setting; a third step of, when the number of deposited particles of a charged-particle beam becomes equal to or larger than a pre-set number of particles or when a coordinate of a position to which a charged-particle beam is irradiated is inconsistent with a coordinate of a pre-set position, stopping the charged-particle beam; and a fourth step at which when a charged-particle beam is stopped, it is judged whether or not irradiation to the whole radiation area is completed, at which if the irradiation is not completed, control is returned to the first step, i is incremented by one, the angle of rotation and field intensity concerning the scanning field generating means, and the energy of the charged-particle beam are modified in a given order, and the first to third steps are thus repeated, and at which if the irradiation is completed, irradiation is terminated.

According to the present invention, there is provided a charged-particle beam irradiation method in which at the fourth step, the angle of rotation of the scanning field generating means is retained at a certain value, the intensity of a field generated by the scanning field generating means and the energy of a charged-particle beam are modified in given order, and the first to third steps are thus repeated.

According to the present invention, there is provided a charged-particle beam irradiation method, in which a scanning field generating means for generating a scanning field composed of a pair of fields effective in bending a charged-particle beam by the same angle in mutually opposite directions is used to shift the spot of the charged-particle beam along a straight line on a plane perpendicular to the axis of incidence of the charged-particle beam, and rotated with the axis of incidence as a center in order to irradiate the charged-particle beam to a radiation area, comprising: a first step of setting the energy of a charged-particle beam to be irradiated according to a coordinate of a position indicating a depth to which a beam is irradiated, $Z_i$ (i=1 that is an initial value), specified in a group of coordinates [($Z_i$, $\theta_{ij}$), i=1, 2, ..., m, j=1, 2, ..., n] defining the radiation area; a second step of specifying the angle of rotation of the scanning field generating means in $\theta_{ij}$ (j=1 that is an initial value) and specifying a set defining a scan pattern that is a characteristic curve relative to time in $I_{ij}(t)$; a third step of irradiating a charged-particle beam according to the setting and specification, driving the scanning field generating means according to the scan pattern that is the characteristic curve relative to time defined by $I_{ij}(t)$, and sweeping the charged-particle beam so as to achieve a given number of scans; a fourth step of judging in parallel with the third step whether or not a coordinate of a position to which a charged-particle beam is irradiated is consistent with a coordinate of a pre-set position; a fifth step of, when the given number of scans have been carried out or when the coordinate of the position at which a charged-particle beam is irradiated is inconsistent with the coordinate of the pre-set position, stopping the charged-particle beam; and a sixth step at which when a charged-particle beam is stopped, it is judged whether or not irradiation to the whole radiation area is completed, at which if the irradiation is completed, irradiation is terminated, at which if the irradiation is not completed, it is judged whether or not the coordinate of the position indicating a depth to which a beam be irradiated, $Z_i$, should be changed to the next value, at which if the coordinate is not changed, j is incremented by one, and control is returned to the second step in order to repeat the second to fifth steps, and at which if the coordinate is changed, i is incremented by one, j is reset to the initial value of 1, and control is returned to the first step in order to repeat the first to fifth steps.

According to the present invention, there is provided a charged-particle beam irradiation method in which the scanning field generating means shifts a beam spot over the radius alone of the radiation area during one beam spill, and $I_{ij}(t)$ $\sqrt{t}$ is adopted as $I_{ij}(t)$ defining the scan pattern that is the characteristic curve relative to time.

DESCRIPTION OF THE PREFERRED EMBODIMENTS

First Embodiment

Figure 1:
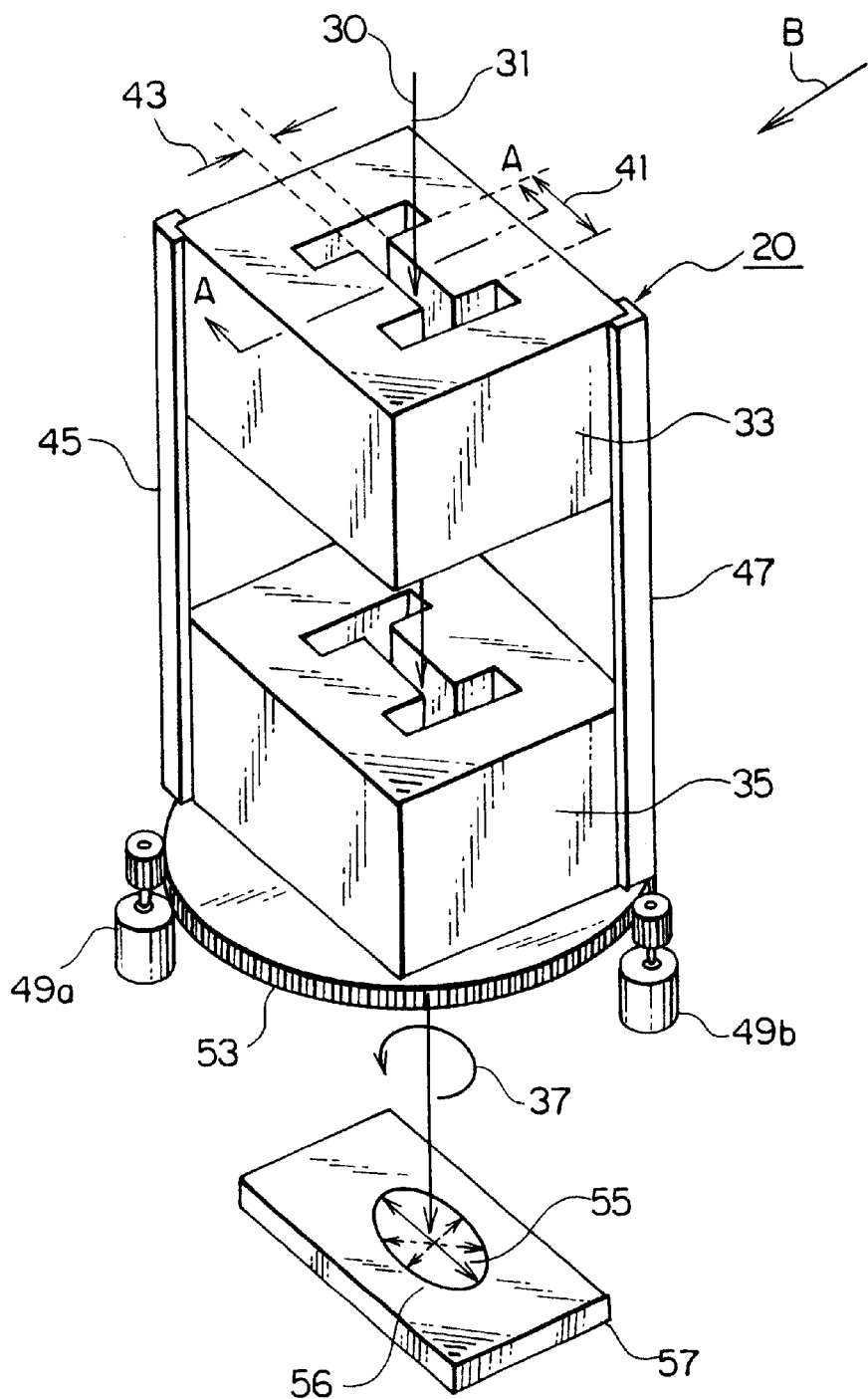
FIG. 1 is a diagram showing the configuration of a charged-particle beam irradiation apparatus in accordance with one embodiment of the present invention.

FIG. 1 is a diagram showing the structure of a charged-particle beam irradiation apparatus in accordance with an embodiment of the present invention. There are shown a charged-particle beam irradiation apparatus 20, an axis of incidence of a beam 30, a charged-particle beam 31 (for example, a proton beam or carbon-particle beam), and two scanning electromagnets 33 and 35 that generate homogeneous magnetic fields which are oriented in mutually opposite directions and whose intensities and effective lengths (length along the axis of incidence 30) are mutually the same, and that are placed with a certain space between them along the axis of incidence 30 of a charged-particle beam. Reference numeral 41 denotes the width of the magnetic poles of the scanning electromagnets 33 and 35, and 43 denotes a gap between magnetic poles. Also shown are linkage frames 45 and 47 for linking the electromagnets 33 and 35.

Figure 2:
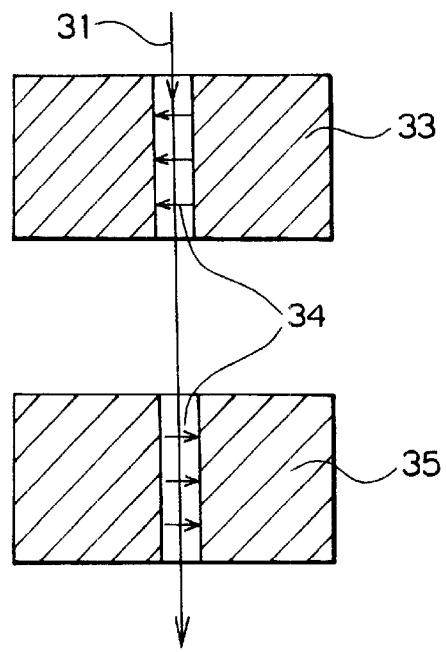
FIG. 2 is a sectional view of scanning electromagnets shown in FIG. 1.
Figure 3:
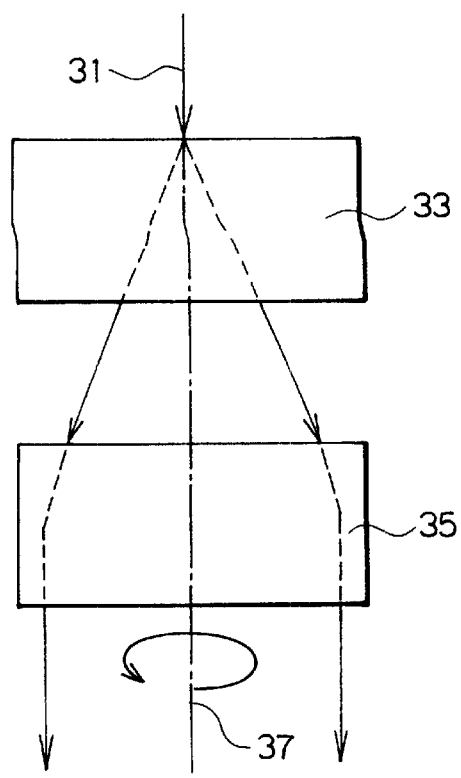
FIG. 3 is a perspective side view of the scanning electromagnets shown in FIG. 1.

There are shown a rotary driving gear 53 for rotating the charged-particle beam irradiation apparatus 20 with an axis of rotation 37 as a center, and motors 49a and 49b for rotating the gear 53. Also shown are an irradiated subject 57 and a radiation area 56. Reference numeral 55 denotes an example of the trajectory of a swept charged-particle beam. FIG. 2 is an A—A sectional view of the charged-particle beam irradiation apparatus shown in FIG. 1. In FIG. 2, reference numeral 34 denotes the directions of magnetic fields generated by the scanning electromagnets 33 and 35. FIG. 3 is a perspective side view of the scanning electrodes 33 and 35 seen in the direction of arrow B in FIG. 1, showing swept states of a charged-particle beam.

Operations will be described below. The incident charged-particle beam 31 is first bent by a certain angle by the scanning electromagnet 33, and then bent in an opposite direction by the same angle by the scanning electromagnet 35 of which magnetic field is oriented in the opposite direction and has the same intensity and effective length as the magnetic field of the scanning electromagnet 33. Consequently, a beam parallel to the original charged-particle beam 31 is irradiated. As a result, the charged-particle beam swept along a scan trajectory that is the sweeping trajectory 55 is always parallel to the incident beam 31.

When the electromagnets 33 and 35 that are united by the linkage frames 45 and 47 are rotated about the axis of rotation 37 by a rotating means composed of the motors 49a and 49b or the like, a two-dimensional radiation area 56 is defined on the irradiated object 57.

Figure 4:
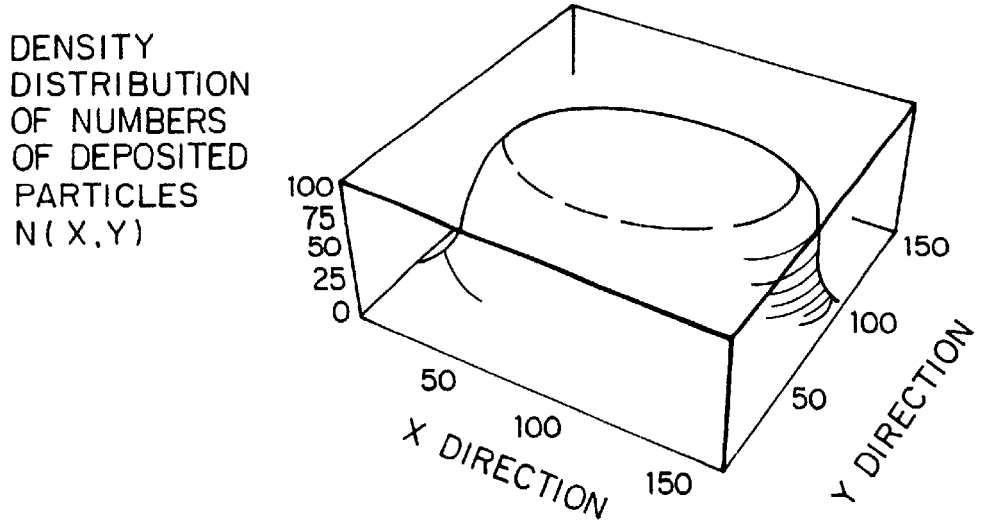
FIG. 4 is a diagram showing a density distribution of numbers of particles observed when a charged-particle beam is irradiated uniformly using a charged-particle beam irradiation apparatus in accordance with the present invention.

Moreover, when the intensity of the beam 31 and the sectional shape thereof are constant, a larger number of particles per unit area are deposited on the center of the radiation area 56 through which the axis of rotation 37 passes than the number of particles to be deposited outside the center. A current flowing into the scanning electromagnets 33 and 35 is controlled so that a sweeping speed will be inversely proportional to a distance by which the beam is swept away from the axis of incidence according to the sweeping trajectory 55. Moreover, a rotation step in units of which rotation is made for the purpose of scan is sufficiently reduced. Consequently, the uniform density distribution of numbers of deposited particles shown in FIG. 4 is attained in the radiation area 56.

Figure 5:
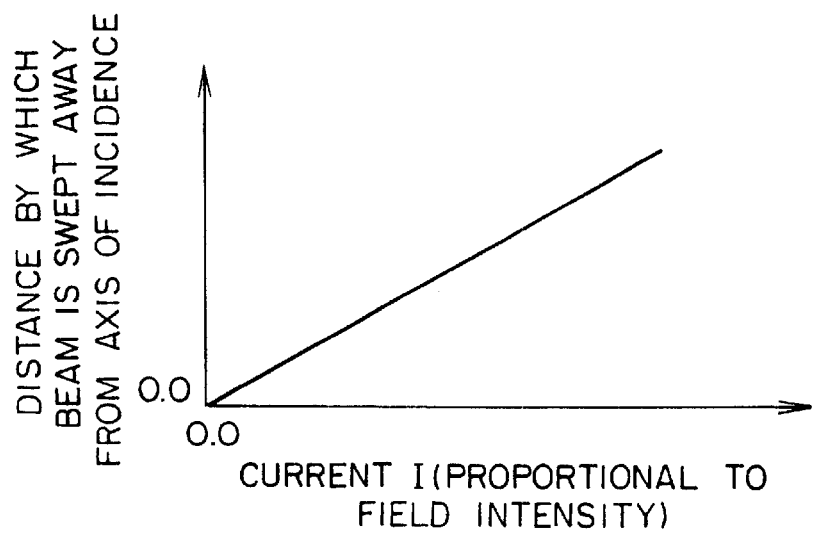
FIG. 5 is a diagram showing the relationship between a distance by which the spot of an incident charged-particle beam is shifted for the purpose of scan and a current flowing into electromagnets, which is established according to the present invention.
Figure 6:
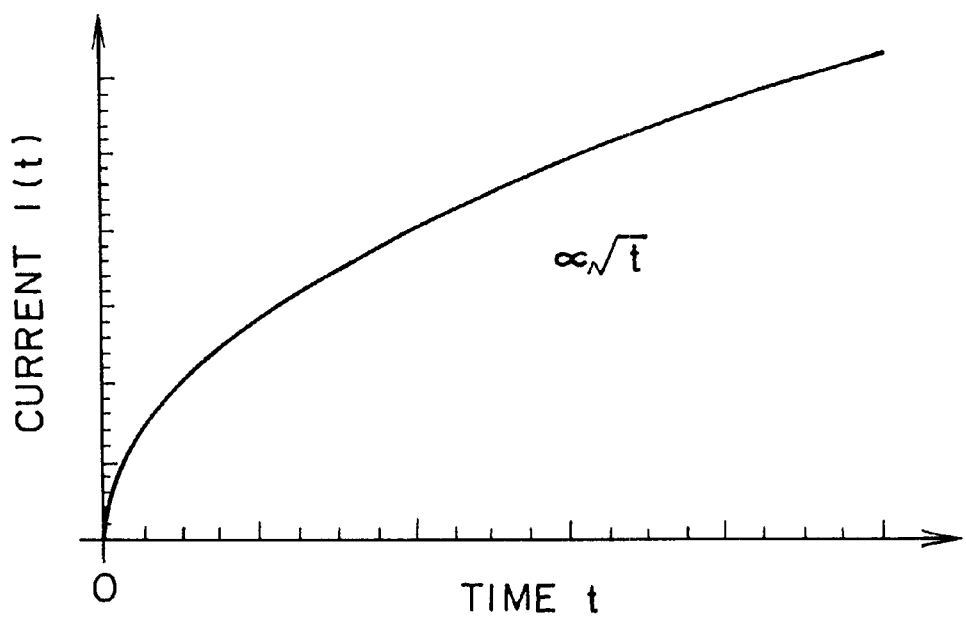
FIG. 6 is a diagram showing a scan pattern that is a characteristic curve relative to time permitting uniform irradiation of a charged-particle beam according to the present invention.
Figure 7:
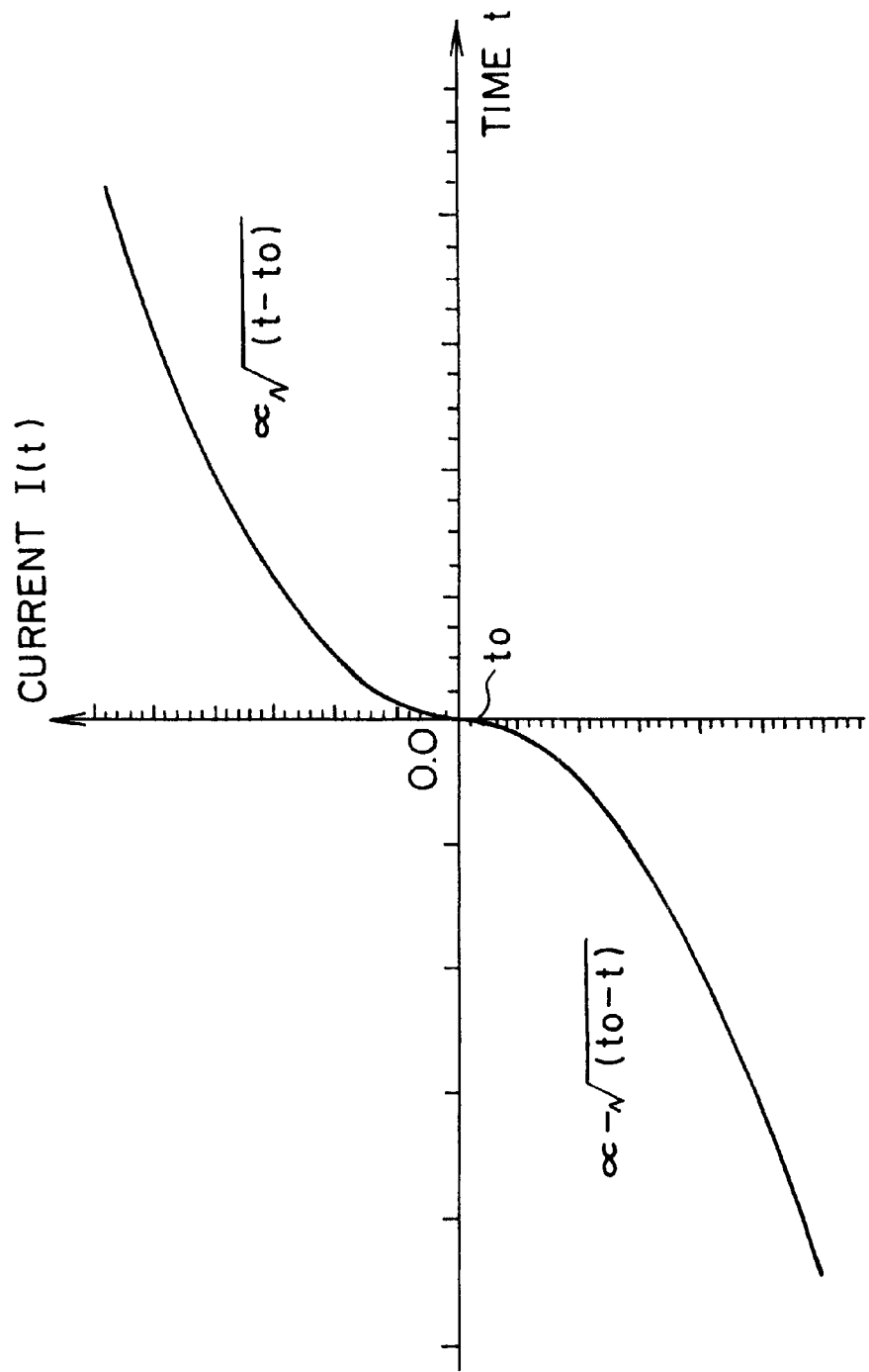
FIG. 7 is a diagram showing a scan pattern that is a characteristic curve relative to time permitting uniform irradiation of a charged-particle beam according to the present invention.

Moreover, since the magnetic fields generated by the scanning electromagnets 33 and 35 are homogeneous, the relationship between the size of a flowing current and a distance by which the beam 31 is swept away from the axis of incidence 30 is, as shown in FIG. 5, a relationship of direct proportion. When a current I(t) flowing into the scanning electromagnets 33 and 35 is controlled as indicated in FIG. 6 or 7, the sweeping speed will be inversely proportional to the distance by which the beam 31 is swept away from the axis of incidence 30.

In the foregoing embodiment, the intensities and effective lengths of the magnetic fields of the scanning electromagnetic 33 and 35 are mutually the same. As long as the beam 31 is bent by the same angle in mutually opposite directions, the intensities and effective lengths of the magnetic fields may be not mutually the same.

Moreover, in the foregoing embodiment, since the charged-particle beam 31 is swept parallel to the axis of incidence 30, the two electromagnets 33 and 35 are employed. As long as a scanning field composed of a pair of fields effective in bending the charged-particle beam 31 by the same angle in mutually opposite directions can be generated, a single electromagnet or a plurality of electromagnets will do. Otherwise, a scanning field generator including a permanent magnet devised to generate a scanning field (for example, a permanent magnet whose spatial location can be varied mechanically) will do.

Figure 8:
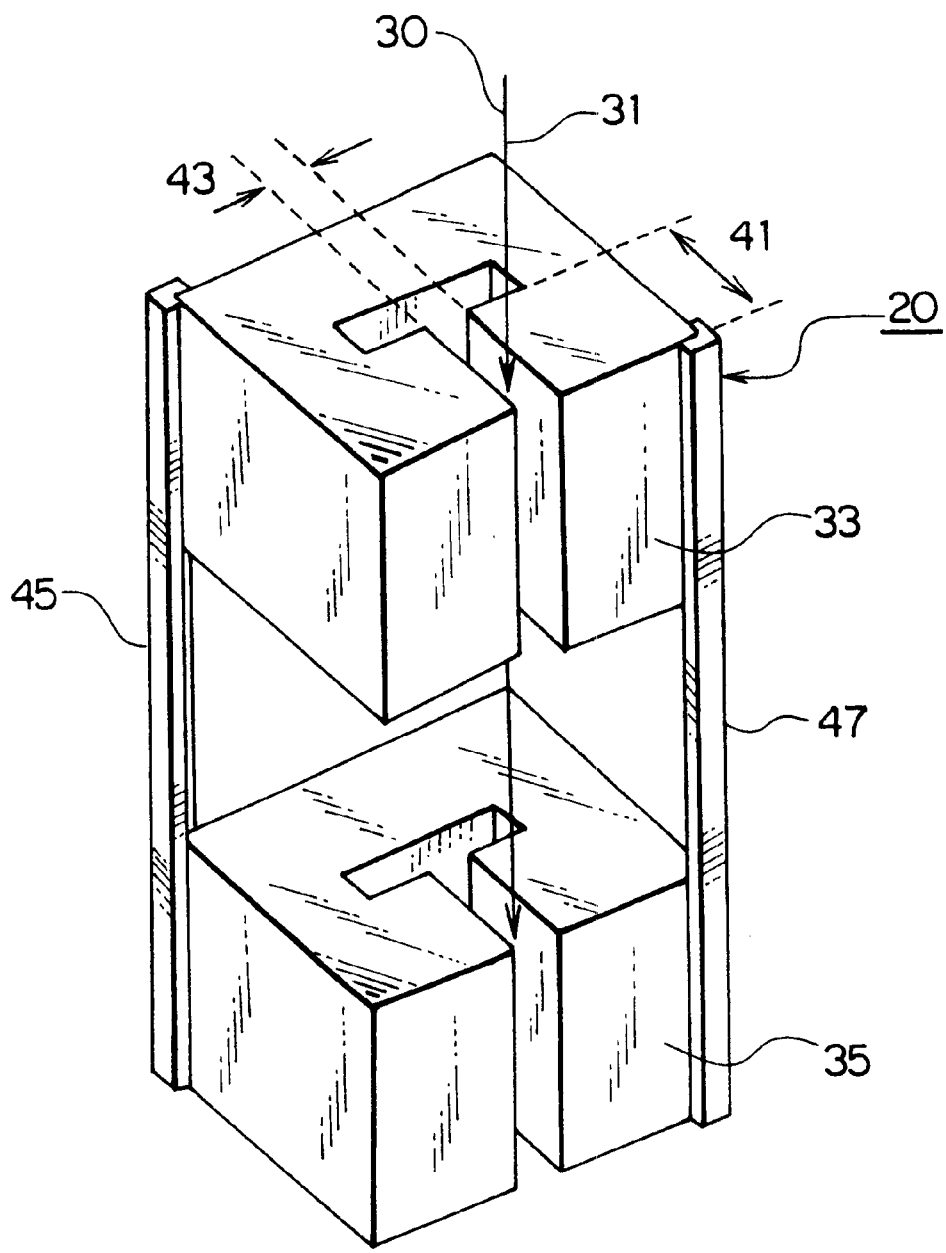
FIG. 8 is a diagram showing another example of the structure of scanning electromagnets employed in a charged-particle beam irradiation apparatus in accordance with the present invention.

FIG. 8 shows an example of a scanning field generating means using two C-shaped scanning electromagnets 33 and 35. As apparent from FIG. 8, the width 41 of the magnetic poles of the electromagnet 33 may be smaller than that of the electromagnet 35. Thus, the overall weight of the irradiation apparatus 20 can be reduced. In the extreme, the section of the magnetic poles of the electromagnet 33 may be shaped like a sector. Furthermore, the gap 43 between the magnetic poles of each of the scanning electromagnets 33 and 35 can be made as small as the size of the section of the incident charged-particle beam 31, because it is unnecessary to sweep the charged-particle beam in a direction traversing the gap 43.

According to this embodiment, a compact charged-particle beam irradiation apparatus having a simple structure and capable of realizing spot scanning in which the spot of a beam parallel to the axis of incidence thereof is shifted in two axial directions can be realized.

Second Embodiment

Figure 9:
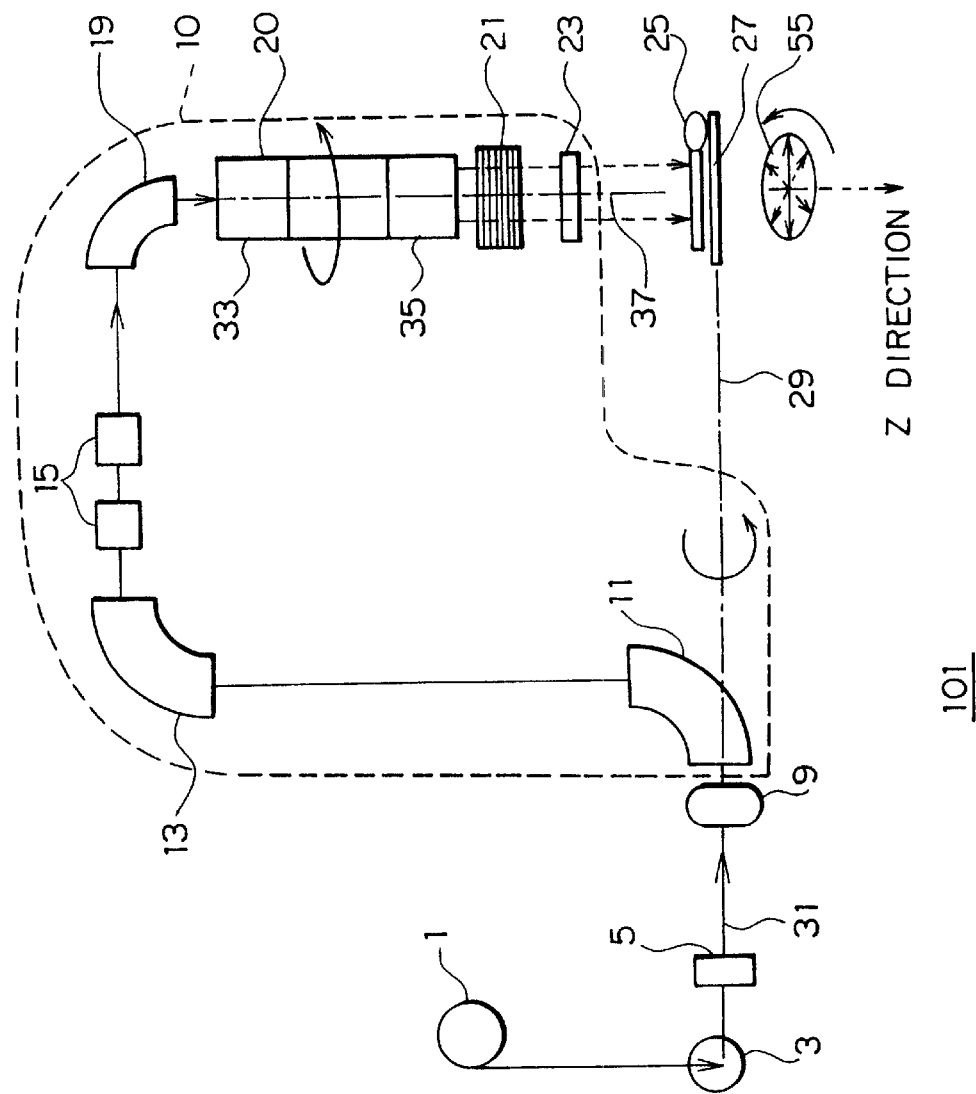
FIG. 9 is a diagram showing the configuration of a charged-particle beam rotary irradiation system in accordance with an embodiment of the present invention.
Figure 10:
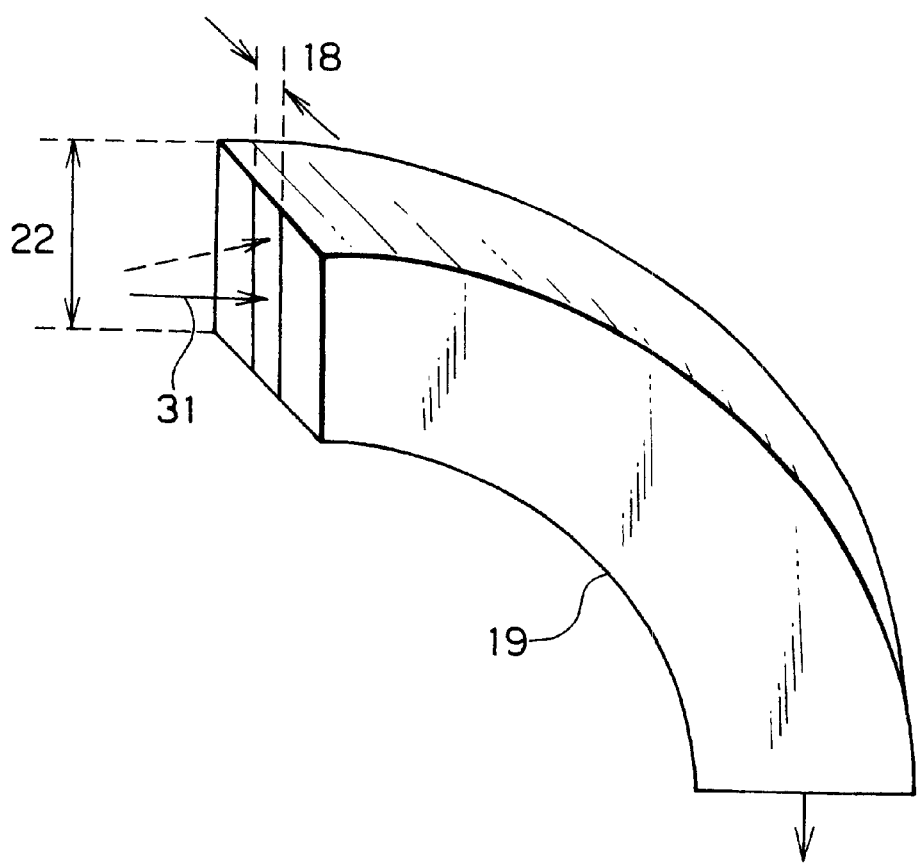
FIG. 10 is a diagram showing the structure of a deflective electromagnet employed in the charged-particle beam rotary irradiation system shown in FIG. 9.

FIG. 9 is a diagram showing the configuration of a charged-particle beam rotary irradiation system in accordance with another embodiment of the present invention which is used as a modality using a charged-particle beam. Components identical or equivalent to those of the conventional system or aforesaid embodiment will bear the same reference numerals, and the description of the components will be omitted. The charged-particle beam rotary irradiation system 101 shown in FIG. 9 has a charged-particle beam irradiation apparatus 20 in accordance with the aforesaid embodiment interposed between a deflective electromagnet 19 and an energy degrader 21. A beam 31 having not been swept falls on the deflective electromagnet 19. The deflective electromagnet 19 is therefore much smaller than a conventional one. Consequently, a patient 25 that is an irradiated subject can be positioned on the axis of rotation 29 of a rotating gantry 10.

Next, operations will be described. In the charged-particle beam rotary irradiation system 101, a charged-particle beam of high energy emanating from an accelerator 1 is delivered to a first-stage energy degrader 5 by means of a transporting electromagnet 3. A charged-particle beam 31 of given energy passed by the energy degrader 5 is bent upward from a horizontal direction by the first deflective electromagnet 11, and then returned to the horizontal direction by a deflective electromagnet 13.

The charged-particle beam is converged by a convergent electromagnet 15, and then routed to the deflective electromagnet 19. As mentioned above, in the system 101 of this embodiment, the beam is not swept in front of the deflective electromagnet 19 but is bent immediately downward by the electromagnet 19 while retaining the thin pencil-like form. Consequently, both the width 22 of the magnetic poles of the deflective electromagnet 19 and the gap 18 between the magnetic poles can be reduced. Eventually, the overall mass and weight of the rotating gantry 10 can be reduced.

Figure 16:
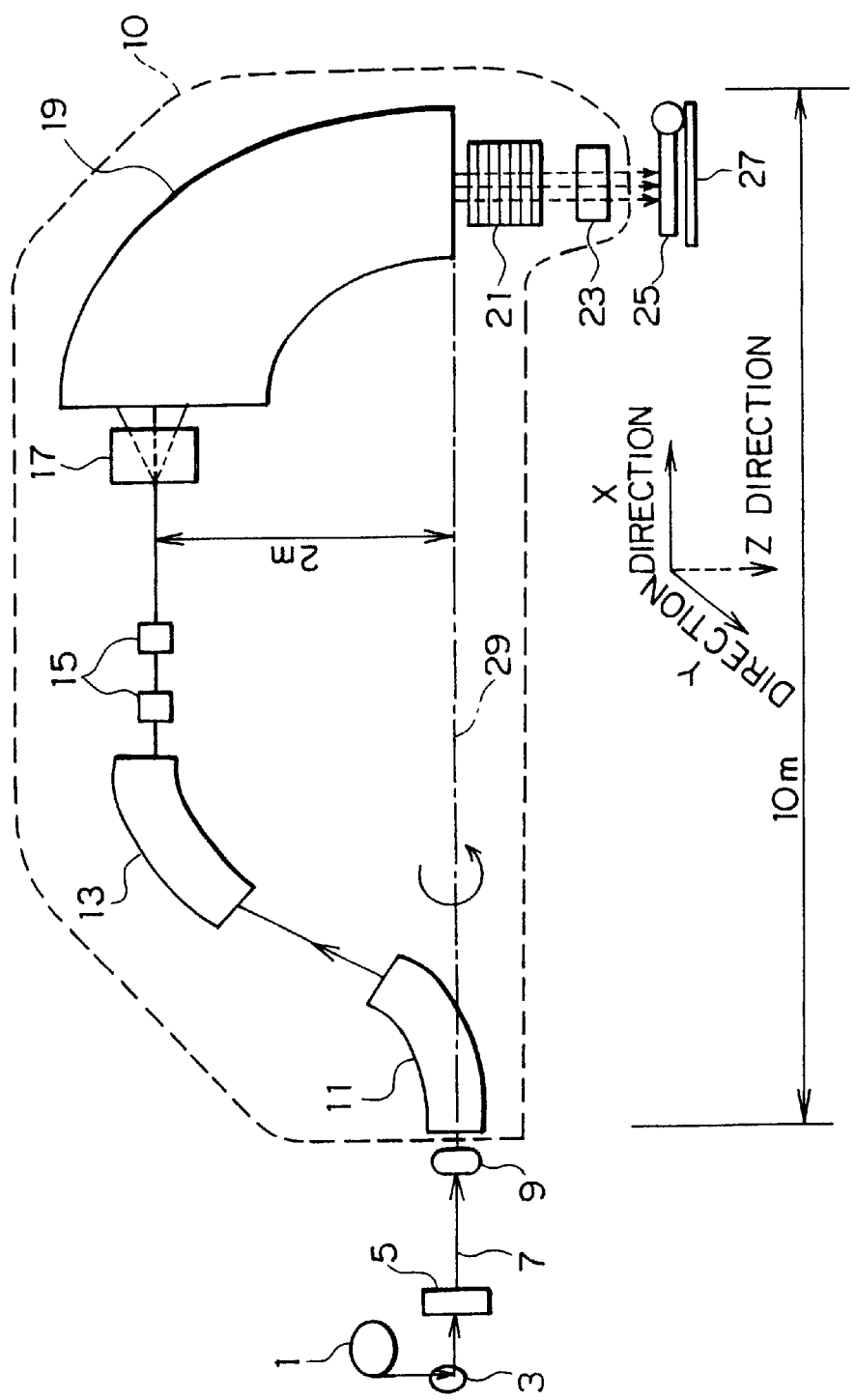
FIG. 16 is a diagram showing the configuration of a charged-particle beam rotary irradiation system in accordance with a prior art.

In the conventional system, the width 22 of the magnetic poles of the deflective electrode 19 is so large as to cover a charged-particle beam swept by the scanning electromagnet 17 shown in FIG. 16, and is therefore several tens of centimeters.

In this embodiment, since the deflective electromagnet 19 is small in size and can therefore be realized readily with a superconducting magnet like the other deflective electromagnets 11 and 13. The rotating gantry 10 can therefore be designed to be more compact and lightweight. Moreover, the charged-particle beam 31 emanating from the deflective electromagnet 19 is swept as described in relation to the first embodiment by the scanning electromagnets 33 and 35 so that the charged-particle beam will always be parallel to the direction of incidence.

In this embodiment, as shown in FIG. 9, spot scanning in which the spot of a beam parallel to the axis of incidence thereof can be shifted in two axial directions can be realized. Consequently, a radiation table 27 on which the patient 25 lies down need not be moved. An effect of improving the accuracy of a position to which a beam is irradiated by a modality is therefore exerted.

Moreover, assuming that a charged-particle beam is a proton beam having as high an energy level as 250 MeV required for treating a deep-seated tumor (the rigidity of a proton relative to a magnetic field is 2.43 Tesla per meter), when a radiation area of 20 cm in diameter is scanned, if the deflective electromagnet 19 is realized with a superconducting magnet, the size of the deflective electromagnet 19 can be set to about 40 cm, and the length from one end of the charged-particle beam irradiation apparatus 20 including the scanning electromagnets 33 and 35 to the other end thereof can be set to about 120 cm. Consequently, the radius of the turning circle of the rotating gantry 10 can be restricted to about 2 m.

As a result, unlike the conventional system, while spot scanning in which the spot of a beam parallel to the axis of incidence thereof is shifted two-dimensionally is realized, the patient 25 can be positioned on the axis of rotation 29 of the rotating gantry 10. The structure of the rotating gantry 10 can therefore be simplified drastically. Furthermore, the weight of a modality including a rotating gantry and generating a proton beam of 250 MeV can be reduced to be a half or less of the weight of the conventional system.

In FIG. 9, the energy degrader 21 and dose/position monitor 23 are incorporated in the rotating gantry 10. Alternatively, the energy degrader 21 and dose/position monitor 23 may be installed separately from the rotating gantry 10.

Third Embodiment

Figure 11:
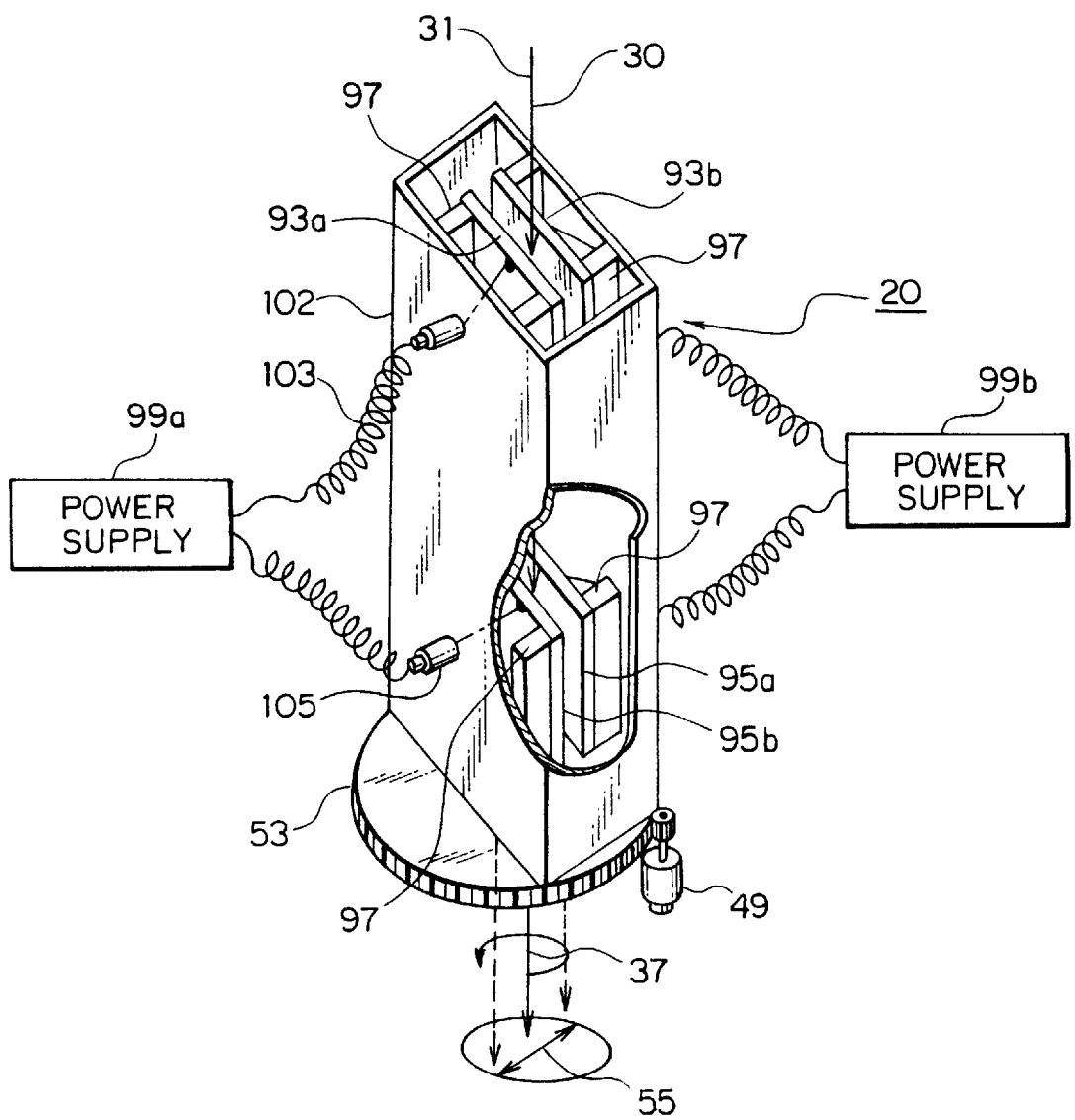
FIG. 11 is a diagram showing the structure of a charged-particle beam irradiation apparatus in accordance with another embodiment of the present invention.

FIG. 11 is a diagram showing a charged-particle beam irradiation apparatus in accordance with another embodiment of the present invention. The charged-particle beam irradiation apparatus shown in FIG. 1 uses electromagnets or the like to generate magnetic fields as a scanning field. In this embodiment, the charged-particle beam irradiation apparatus 20 generates electric fields as a scanning field using two pairs of electrodes that are mutually facing with a gap between them.

In FIG. 11, there are shown electrodes 93a, 93b, 95a, and 95b, insulators 97 for supporting the electrodes, a box 102 made of a stainless steel for supporting the electrodes and insulators, power supplies 99a and 99b, cables 103 over which a voltage is supplied to the electrodes 93a, 93b, 95a, and 95b, cable connectors 105, and a motor 49 for rotating the box 102 via a rotary driving gear 53 having the box mounted thereon.

The electrodes 93a, 93b, 95a, and 95b generate electric fields oriented in mutually opposite directions, whereby an incident charged-particle beam 31 is bent by the same angle in the mutually opposite directions. A beam parallel to the direction of incidence thereof is therefore swept all the time. By rotating the whole box 102, spot scanning in which the spot of a beam parallel to the axis of incidence thereof is shifted two-dimensionally can be realized in the radiation area.

Moreover, the charged-particle beam irradiation apparatus of this embodiment may be employed as the charged-particle beam irradiation apparatus 20 included in the charged-particle beam rotary irradiation system of the second embodiment.

Fourth Embodiment

Figure 12:
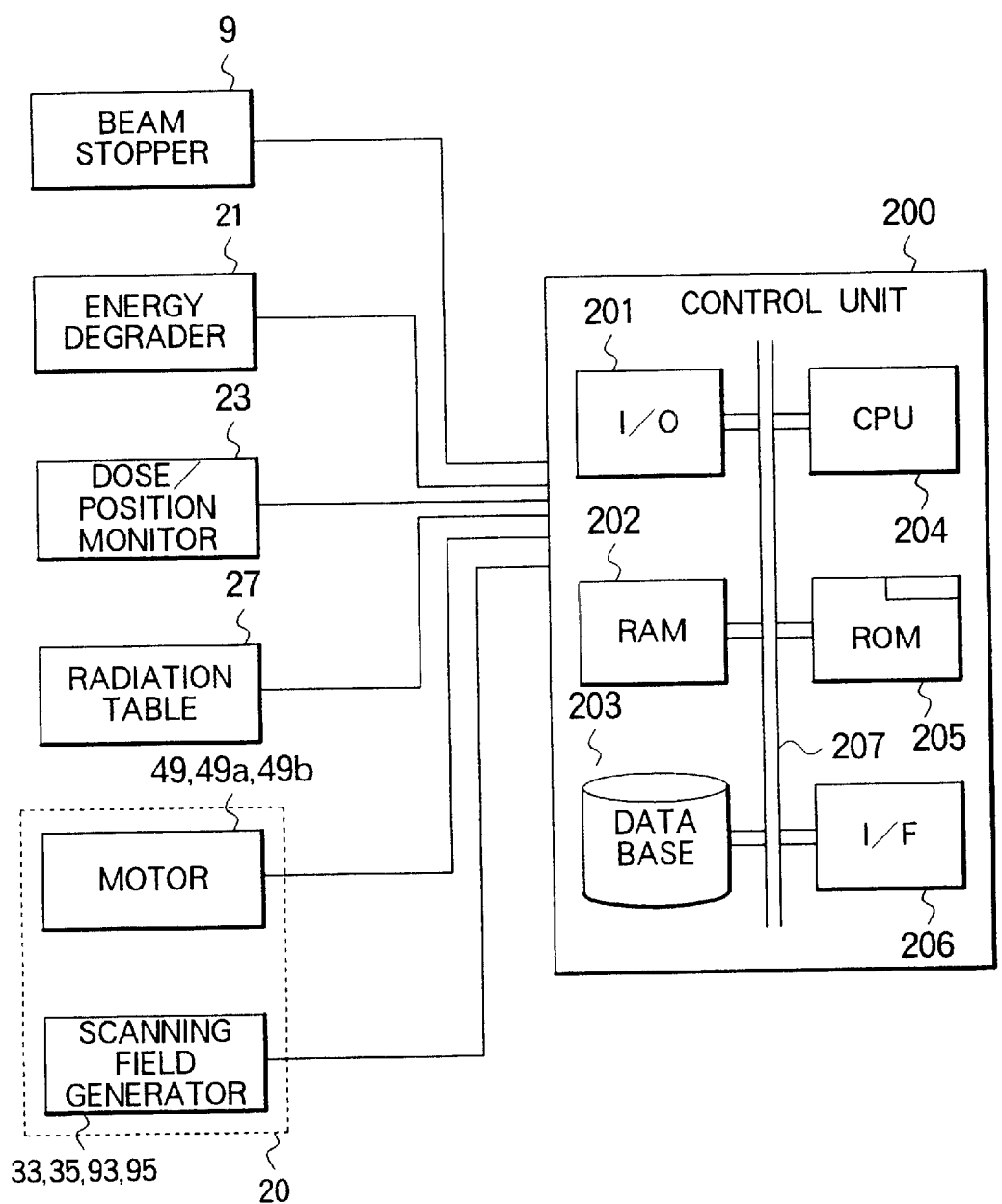
FIG. 12 is a diagram showing the configuration of especially a control system in a charged-particle beam rotary irradiation system in accordance with another embodiment of the present invention.

FIG. 12 ia a diagram showing the configuration of a control portion of a charged-particle beam rotary irradiation system in accordance with the present invention. The control portion is responsible for control of, for example, the charged-particle beam rotary irradiation system shown in FIG. 9. A portion involved in controlling scan is extracted.

In FIG. 12, there are shown a control unit 200 formed, for example, with a personal computer, an input/output (hereinafter I/O) control unit 201, a RAM 202 serving as a temporary memory, a database 203 for storing various kinds of information including the setting conditions for beam irradiation, a CPU 204 serving as a processor, a ROM 205 for storing a control program and others, an interface 206 for providing interface with another system, and a bus 207 over which the components are interconnected. Connected to the control unit 200 are a beam stopper 9, an energy degrader 21, a dose/position monitor 23, a radiation table 27, motors 49, 49a, and 49b which are incorporated in the irradiation apparatus 20, and a scanning field generator equivalent to electromagnets 33 and 35 or electrodes 93a, 93b, 95a, and 95b.

Figure 13:
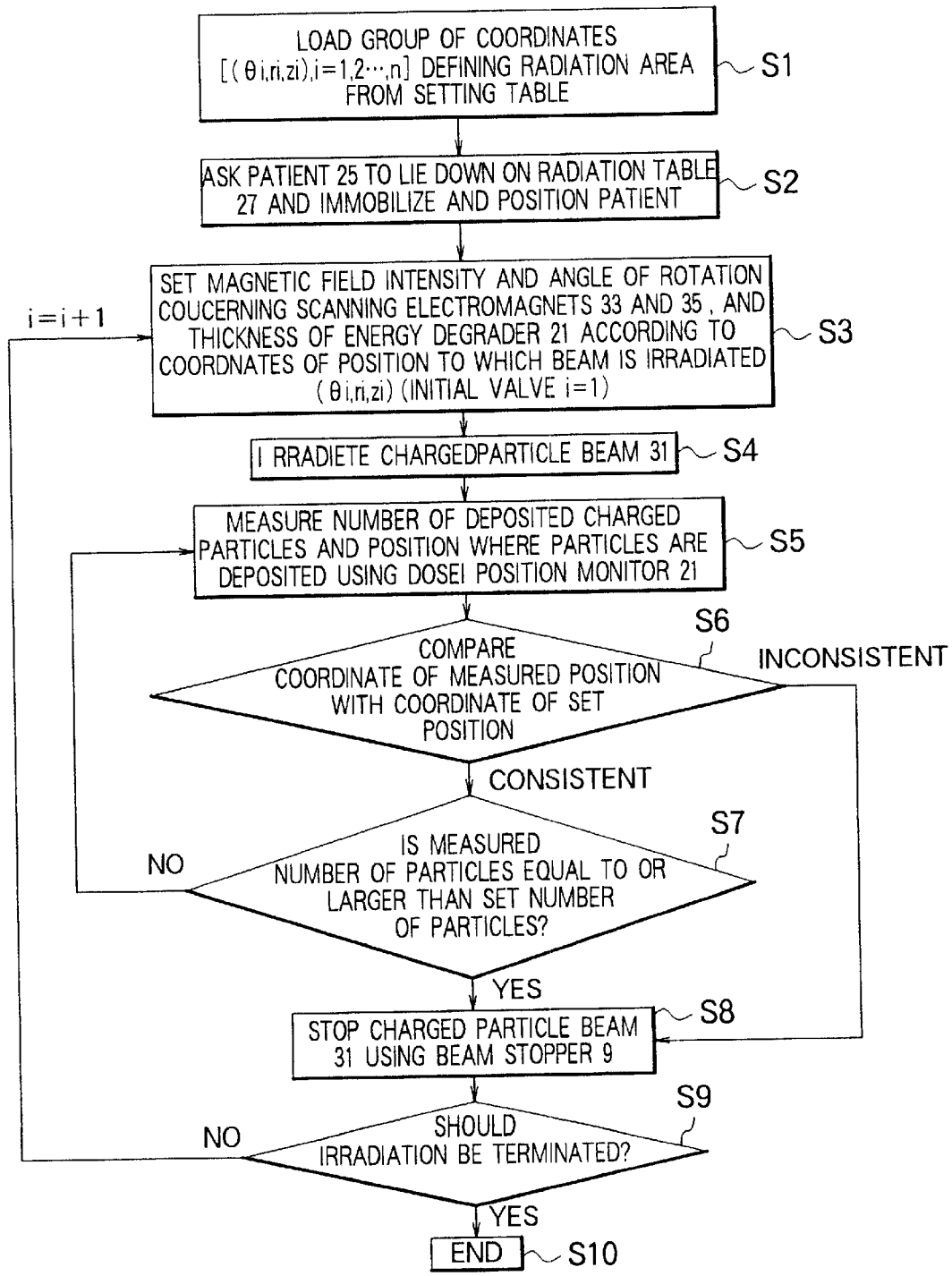
FIG. 13 is a flowchart describing an example of operations performed by the control system in the charged-particle beam rotary irradiation system in accordance with the present invention.

FIG. 13 is a flowchart describing a control sequence employed in the control unit 200. The control unit 200 operates according to a program P describing the control sequence and residing in the ROM 205.

Referring to FIGS. 9, 12, and 13, a control operation will be described. First, a group of three-dimensional coordinates of positions [Pi: i=1, 2, . . . , n] defining a radiation area of the patient 25, for example, [(θi, ri, Zi), i=1, 2, . . . , n] (θ indicates an angular direction, r indicates a radial direction, and Z indicates a depth direction) in the system of cylindrical coordinates is loaded from a setting table created in advance to the control unit 200 for controlling an irradiation system via the interface 206 (step S1).

Thereafter, the patient 25 is asked to lie down on the radiation table 27, and then immobilized and positioned (step S2). The step S2 may be achieved by positioning the movable radiation table 27 or may require human labor.

Thereafter, the thickness of the energy degrader 21 is set according to a coordinate of a position to which a beam is irradiated, Zi (i=1 that is an initial value). The angle of rotation and field intensity concerning the scanning electromagnets 33 and 35 are set according to the coordinates of the position to which a beam is irradiated (θi, ri) (step S3).

Thereafter, the charged-particle beam 31 is irradiated (step S4), and the number of incident particles contained in the charged-particle beam 31 and a position where the particles are deposited are measured using the dose/position monitor 23 (step S5). The coordinate of the position measured at step S5 is compared with the coordinate of the position set at step S3 (step S6). If they are inconsistent with each other, control is passed to step S8 of stopping the beam 31 which will be described later. If the result of comparison performed at step S6 reveals that the coordinate of the measured position is consistent with the coordinate of the set position, it is judged whether or not an integrated value of numbers of particles measured at step S5 is equal to or larger than a pre-set number of particles at a given position (step S7). If the integrated value does not exceed, control is returned to step S5. If the integrated value exceeds, the charged-particle beam 31 is stopped using the beam stopper 9 (step S8).

It is then judged whether or not irradiation should be terminated (step S9). If irradiation is continued, i is incremented by one, and control is returned to step S3. If irradiation should be terminated, it is terminated at step S10.

According to the foregoing procedure, steps S3 to S9 are executed repeatedly by assigning values ranging from 1 to n to i. Thus, a given number of particles [Ni, i=1, 2, . . . , n] are deposited on all spots in the three-dimensional radiation area which are described as a group of coordinates of positions [(θi, ri, Zi), i=1, 2, . . . , n].

If the orders of steps S1 and S2 were switched, the same effect would be exerted. Moreover, according to the aforesaid procedure, the rotating speed of the scanning electromagnets 33 and 35 is lower than a scanning speed dependent on a magnetic field intensity or a scanning speed determined by the energy degrader 21. When scanning a radiation area in other two directions is carried out earlier with an angle of rotation θi held constant, an overall time required for irradiation can be shortened.

In the above description, as a means for changing an energy level, the thickness of the energy degrader 21 is changed. Any other means for changing an energy level, for example, a synchrotron particle accelerator may be employed. Moreover, a means for stopping a charged-particle beam has been described by taking the beam stopper 9 for instance. Any other beam stopping means (for example, stopping a particle accelerator) may be employed.

Furthermore, the system of cylindrical coordinates have been adopted as an example of a system of coordinates used to express a group of three-dimensional coordinates of positions [Pi : i=1, 2, . . . , n] defining a radiation area. Alternatively, any other system of coordinates that is a variant of the system of cylindrical coordinates may be adopted. In the above description, the irradiation apparatus 20 including the scanning electromagnets 33 and 35 is used as a means for sweeping a charged-particle beam. This embodiment is not limited to the irradiation apparatus 20. Any other means for sweeping a charged-particle beam, for example, an irradiation apparatus 20 including the scanning electrodes employed in the third embodiment will do.

Fifth Embodiment

Figure 14:
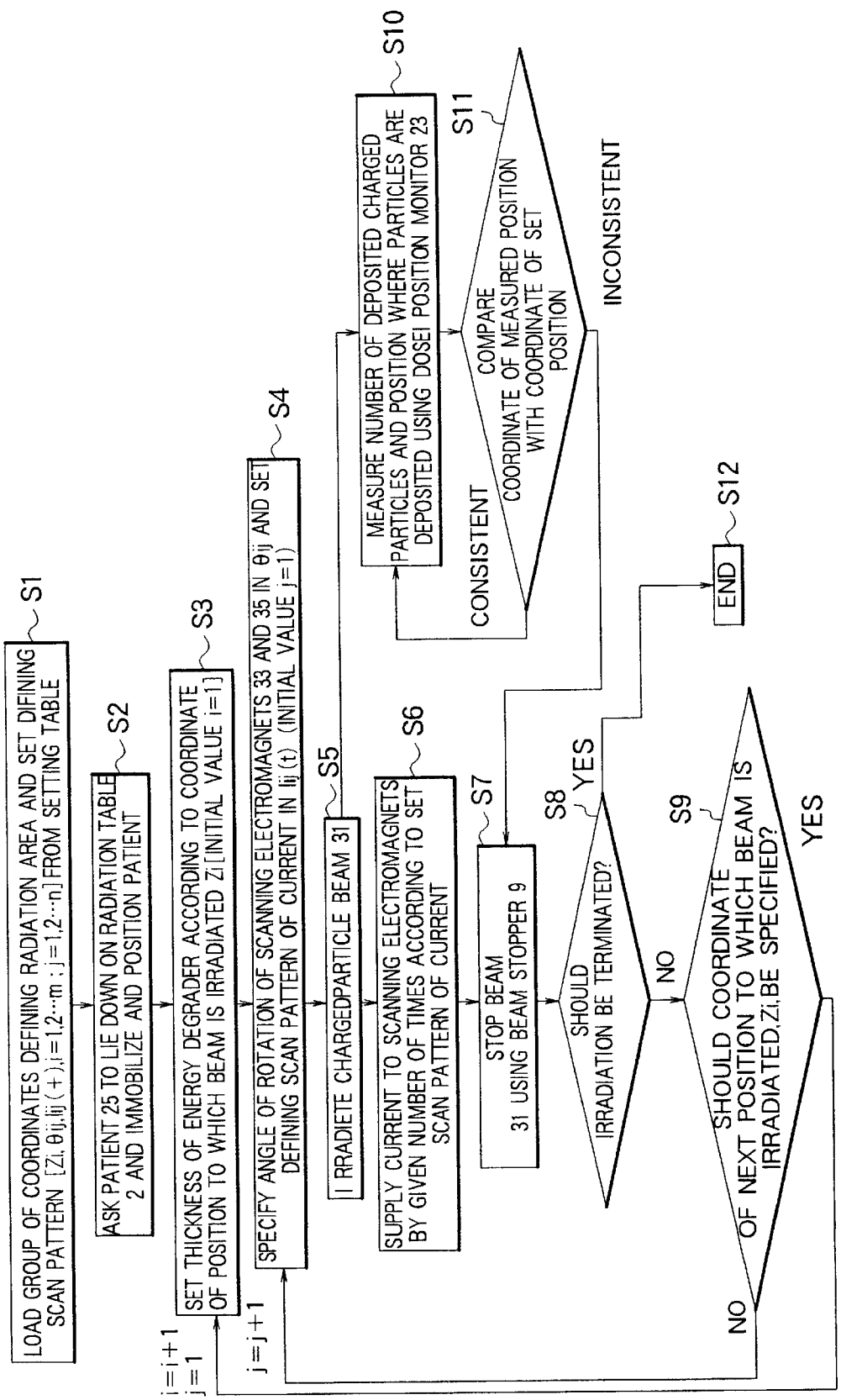
FIG. 14 is a flowchart describing another example of operations performed by the control system in the charged-particle beam rotary irradiation system in accordance with the present invention.

FIG. 14 is a flowchart describing a control sequence employed in the control unit 200 shown in FIG. 12 according to another method. Like the fourth embodiment, assume that the initial energy level of the charged-particle beam 31 is held constant by setting the energy degrader 5 to a certain thickness.

Referring to FIGS. 9, 12, and 14, a control operation will be described. First, a group of coordinates of positions [(Zi, θij), i=1, 2, . . . m, j=1, 2, . . . , n] defining a radiation area of the patient 25 and a set [Iij(t), j=1, 2, . . . , n] defining a scan pattern that is a characteristic curve relative to time are loaded from a setting table created in advance to the control unit 200 via the interface 206 (step S1). These coordinates of positions that are the coordinates of positions, Zi, indicating depths, the angles of rotation, θij, at the depths, and the set, Iij(t), defining the scan pattern that is the characteristic curve relative to time concerning scan in a direction of a diameter or radius at the angles are used to express a three-dimensional radiation area.

Thereafter, the patient 25 is asked to lie down on the radiation table 27, and immobilized and positioned. This step S2 may be achieved by positioning the movable radiation table 27 or may require human labor. The thickness of the energy degrader 21 is set according to a coordinate of a position to which a beam is irradiated, Zi (i=1 that is an initial value) (step S3). The angle of rotation of the scanning electromagnets 33 and 35 is specified in θij (j=1 that is an initial value), and a set defining a scan pattern according to which a current is supplied to the electromagnets is specified in Iij(t).

The charged-particle beam 31 is then irradiated (step S5). A current is supplied by a given number of times according to the scan pattern of a current flowing into the scanning electromagnets 33 and 35 which is set at step S4. Specifically, for example, a current is supplied to the scanning electromagnets 33 and 35 according to the pre-set scan pattern of a current, which is defined by Iij(t), during scan of a radius or diameter of a radiation area expressed in, for example, the system of cylindrical coordinates (step S6). When the intensity of an incident charged-particle beam varies with the passage of time, the scan pattern of a current is controlled on the basis of a time-passing increase rate of the number of charged particles to be measured in real time by the dose/position monitor 23 at step S10 that will be described later. Thus, the desired distribution of numbers of of particles is attained.

When a given number of scans are completed, the beam 31 is stopped using the beam stopper 9 (step S7). It is then judged whether or not irradiation should be terminated (step S8). If irradiation should be terminated, control is jumped to step S12 that will be described later. If it is judged at step S8 that irradiation is continued, it is judged whether or not a coordinate of a position indicating the next depth, Zi, should be specified (step S9). If the coordinate of the next position Zi is specified, i is incremented by one and j is reset to the initial value of 1. Control is then returned to step S3. If the coordinate of the next position Zi is not specified, j is incremented by one and control is returned to step S4.

Thus, steps S3 to S9 and steps S3 to S8 are repeatedly executed by assigning values ranging from 1 to m to i and values ranging from 1 to n to j. The given radiation area is thus irradiated.

The number of deposited charged particles and a position where the particles are deposited are measured by the dose/position monitor 23 during irradiation (step S10). The coordinate of the position measured at step S10 is compared with the coordinate of the position, θij, set at step S4. If they are consistent with each other, control is returned to step S10. If they are inconsistent with each other, the charged-particle beam 31 is stopped using the beam stopper 9 (step S8).

Figure 15:
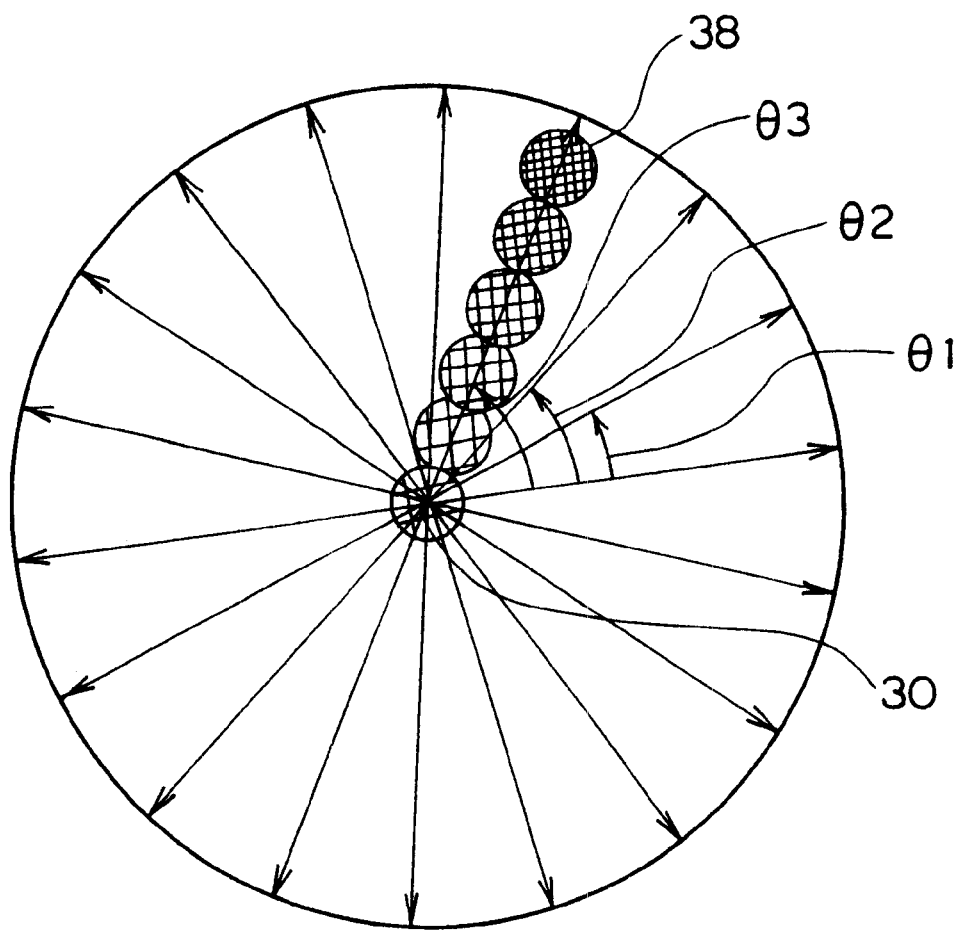
FIG. 15 is a diagram showing the way of shifting the spot of a charged-particle beam in a radial direction for the purpose of scan according to the present invention.

Now, the scan pattern defined by Iij(t) will be described. FIG. 15 shows an example of a trajectory along which the spot of the charged-particle beam 31 is shifted according to the charged-particle beam irradiation method of this embodiment. Reference numeral 38 denotes the spot of the charged-particle beam 31 shifted. FIG. 15 is concerned with scan over the radius of a radiation area. Alternatively, the radiation area can be scanned over the diameter thereof.

Moreover, according to the charged-particle beam irradiation method of this embodiment, when the number of particles of the incident charged-particle beam 31 per unit time and the shape of the beam remain unchanged, the scan pattern shown in FIG. 6 (scan over a radius) or FIG. 7 (scan over a diameter) may be adopted as the scan pattern defined by Iij(t). In this case, when a radiation area is scanned as shown in FIG. 15, the flat density distribution of numbers of particles like the one shown in FIG. 4 can be attained.

When Iij(t) defining the scan pattern is changed to a set, the set proportional to a square root of a variable t of time like the one defining the scan patter shown in FIG. 6 or 7, a sweeping speed at which a beam is swept as shown in FIG. 15 can be controlled so that it will be inversely proportional to the distance from the center axis of rotation. This is attributable to the fact that a current flowing into the electromagnets 33 and 35 and a distance by which a beam is swept away from the axis of incidence thereof have, as shown in FIG. 5, the relationship of inverse proportion. The relationship of inverse proportion between the sweeping speed and the distance from the center axis of rotation leads to the flat density distribution of numbers of particles shown in FIG. 4.

Compared with when a radiation area is scanned over a diameter thereof, when the radiation area is scanned over a radius thereof in steps of an angle of rotation with the axis of incidence 30 shown in FIG. 15 as a center, the width 41 of the magnetic poles of the scanning electromagnets 33 and 35 shown in FIG. 1 and the length thereof in the direction of a beam can be shortened. Consequently, this results in a compact and lightweight irradiation apparatus.

In the above description, the irradiation apparatus 20 including the scanning electromagnets 33 and 35 is used as a means for sweeping a charged-particle beam. This embodiment is not limited to the irradiation apparatus. Any other means for sweeping a charged-particle beam, for example, an irradiation apparatus 20 including the scanning electrodes employed in the third embodiment will do. In this case, a voltage to be applied to the irradiation apparatus 20 is varied according to the scan pattern Iij(t). That is to say, the scan pattern Iij(t) indicates a voltage as a function of time.

The usage of the systems and method of the embodiments is not limited to the usage as a modality using a charged-particle beam but can apply to a wide range of fields, in which irradiation or injection of a charged-particle beam is required, including a field of semiconductors and a field of materials.

As described so far, according to the present invention, a charged-particle beam irradiation apparatus comprises a scanning field generating means for generating a scanning field composed of a pair of fields effective in bending a charged-particle beam by the same angle in mutually opposite directions, and a rotating means for rotating the scanning field generating means with the axis of incidence of the charged-particle beam as a center. Consequently, there is provided a compact charged-particle beam irradiation apparatus realizing spot scanning in which the spot of a beam parallel the axis of incidence thereof is shifting in two axial directions.

Moreover, the scanning field generating means generates magnetic fields. Consequently, there is provided a compact charged-particle beam irradiation apparatus for generating a scanning magnetic field.

Moreover, the scanning field generating means generates electric fields. Consequently, there is provided a compact charged-particle beam irradiation apparatus for generating a scanning electric field.

Moreover, according to the present invention, a charged-particle beam rotary irradiation system comprises: a deflecting means for deflecting a charged-particle beam so that the charged-particle beam will be perpendicular to a radiation plane; a charged-particle beam irradiation apparatus that includes a scanning field generator, placed downstream of the deflecting means, for generating a scanning field composed of a pair of fields effective in bending the charged-particle beam by the same angle in mutually opposite directions, and a rotator for rotating the scanning field generator with the axis of incidence of the charged-particle beam as a center, and that sweeps the charged-particle beam deflected by the deflecting means for the purpose of scan; a charged-particle beam energy adjusting means interposed between the charged-particle beam irradiation apparatus and an irradiated subject; and a rotary motion means for rotating at least the deflecting means and charged-particle beam irradiation apparatus in one united body. Thus, since a compact charged-particle beam irradiation apparatus capable of realizing spot scanning in which the spot of a beam parallel to the axis of incidence thereof is shifted in two axial directions is employed, an irradiated subject need not be moved. Moreover, since the charged-particle beam irradiation apparatus is placed downstream of a deflecting means, the deflecting means can be designed compactly. This results in a compact charged-particle beam rotary irradiation system.

Moreover, according to the present invention, in the charged-particle beam rotary irradiation system, the charged-particle beam falls on the deflecting means from the direction of the axis of rotation of the rotary motion means. The deflecting means includes three deflective electromagnets for deflecting the incident charged-particle beam three times by 90° with respect to a direction parallel to a radiation plane so that the charged-particle beam will be perpendicular to the radiation plane. The irradiated subject is positioned on the axis of rotation of the rotary motion means. Thus, there is provided a charged-particle beam rotary irradiation system in which the rotary motion means can be controlled readily.

Moreover, according to the present invention, in the charged-particle beam rotary irradiation system, the deflective electromagnets of the deflecting means are realized with superconducting electromagnets. Consequently, there is provided a more compact charged-particle beam rotary irradiation system.

Moreover, according to the present invention, a charged-particle beam irradiation system comprises: a charged-particle beam irradiation apparatus that includes a scanning field generator for generating a scanning field composed of a pair of fields effective in bending a charged-particle beam by the same angle in mutually opposite directions, and a rotator for rotating the scanning field generator with the axis of incidence of the charged-particle beam as a center; a charged-particle beam energy adjusting means, interposed between the charged-particle beam irradiation apparatus and an irradiated subject, for adjusting the energy of a charged-particle beam; a dose/position measuring means, interposed between the charged-particle beam irradiation apparatus and irradiated subject, for monitoring the dose and position of an irradiated charged-particle beam; a means for stopping a charged-particle beam; and a control means, connected to the respective means, for controlling scan. The control means includes: a first means for setting the angle of rotation and field intensity concerning the scanning field generator, and the energy of a charged-particle beam according to a group of coordinates [Pi : i=1, 2, . . . , n] (i=1 that is an initial value) defining a radiation area; a second means for irradiating a charged-particle beam according to the setting; a third means for, when the number of deposited particles of a charged-particle beam becomes equal to or larger than a pre-set number of particles or when a coordinate of a position to which the charged-particle beam is irradiated is inconsistent with a coordinate of a pre-set position, stopping the charged-particle beam; and a fourth means that when a charged-particle beam is stopped, judges whether or not irradiation to the whole radiation area is completed, that if the irradiation is not completed, increments i by one, modifies the angle of rotation and field intensity concerning the scanning field generator, and the energy of a charged-particle beam in given order, and thus actuates the first to third means repeatedly, and that if the irradiation is completed, terminates irradiation. Consequently, there is provided a charged-particle beam irradiation system capable of irradiating a charged-particle beam by an accurate dose to an accurate position without the necessity of moving the irradiated subject.

Moreover, according to the present invention, in the charged-particle beam irradiation system, the fourth means retains the angle of rotation of the scanning field generator at a certain value, the intensity of a field generated by the scanning field generator and the energy of a charged-particle beam are modified in given order, and thus the first to third means are actuated repeatedly. Consequently, there is provided a charged-particle beam irradiation system in which the total time required for irradiation is shortened by reducing the frequency of adjusting the angle of rotation that varies slowly.

Moreover, according to the present invention, a charged-particle beam irradiation system comprises: a charged-particle beam irradiation apparatus that includes a scanning field generator for generating a scanning field composed of a pair of fields effective in bending a charged-particle beam by the same angle in mutually opposite directions, and a rotator for rotating the scanning field generator with the axis of incidence of the charged-particle beam as a center, and that sweeps the charged-particle beam for the purpose of scan; a charged-particle beam energy adjusting means, interposed between the charged-particle beam irradiation apparatus and an irradiated subject, for adjusting the energy of a charged-particle beam; a dose/position measuring means, interposed between the charged-particle beam irradiation apparatus and irradiated subject, for monitoring the does and position of an irradiated charged-particle beam; a means for stopping a charged-particle beam; and a control means, connected to the respective means, for controlling scan. The control means includes: a first means for setting the energy of a charged-particle beam to be irradiated according to a coordinate of a position indicating a depth to which a beam is irradiated, Zi (i=1 that is an initial value), specified in a group of coordinates [(Zi, θij), i=1, 2, . . . , m, j=1, 2, . . . , n] defining a radiation area; a second means for specifying the angle of rotation of the scanning field generator in θij (j=1 that is an initial value) and specifying a set defining a scan pattern that is a characteristic curve relative to time in Iij(t); a third means for irradiating a charged-particle beam according to the setting and specification, driving the scanning field generator according to the scan pattern that is the characteristic curve relative to time defined by Iij(t), and thus shifting the spot of the charged-particle beam so as to achieve a given number of scans; a fourth means for judging in parallel with the scans achieved by the third means whether or not a coordinate of a position to which a charged-particle beam is irradiated is consistent with a coordinate of a pre-set position; a fifth means for, when the given number of scans have been carried out or when the coordinate of the position to which a charged-particle beam is irradiated is inconsistent with the coordinate of the pre-set position, stopping the charged-particle beam; and a sixth means that when a charged-particle beam is stopped, judges whether or not irradiation to the whole radiation area is completed, that if the irradiation is completed, terminates irradiation, that if the irradiation is not completed, judges whether or not the coordinate of the position indicating a depth to which a charged-particle beam is irradiated, Zi, should be changed to the next value, that if the coordinate is not changed, increments j by one, and actuates the second to fifth means repeatedly, that if the coordinate is changed, increments i by one, resets j to the initial value 1, and actuates the first to fifth means repeatedly. Consequently, there is provided a charged-particle; beam irradiation system capable of irradiating a charged-particle beam by an accurate dose to an accurate position without the necessity of moving the irradiated subject.

Moreover, according to the present invention, in the charged-particle beam irradiation system, Iij(t)$\sqrt{t}$ is adopted as Iij(t) defining the scan pattern, that is, the characteristic curve relative to time to be followed by the scanning field generator. Consequently, there is provided a charged-particle beam irradiation system capable of irradiating a charged-particle beam more uniformly.

Moreover, according to the present invention, a charged-particle beam irradiation method, in which a scanning field generating means for generating a scanning field composed of a pair of fields effective in bending a charged-particle beam by the same angle in mutually opposite directions is used to sweep the charged-particle beam along a straight line on a plane perpendicular to the axis of incidence of the charged-particle beam for the purpose of scan, rotated with the axis of incidence as a center in order to irradiate the charged-particle beam to a radiation area, comprises a first step of setting the angle of rotation and field intensity concerning the scanning generating means, and the energy of a charged-particle beam according to a group of coordinates [Pi : i=1, 2, . . . , n] (i=1 that is an initial value) defining the radiation area; a second step of irradiating a charged-particle beam according to the setting; a third step of, when the number of deposited particles of a charged-particle beam becomes equal to or larger than a pre-set number of particles or when a coordinate of a position to which a charged-particle beam is irradiated is inconsistent with a coordinate of a pre-set position, stopping the charged-particle beam; and a fourth step at which when a charged-particle beam is stopped, it is judged whether or not irradiation to the whole radiation area is completed, at which if the irradiation is not completed, control is returned to the first step, i is incremented by one, the angle of rotation and field intensity concerning the scanning field generating means, and the energy of a charged-particle beam are modified in given order, and thus the first to third steps are repeated, and at which if the irradiation is completed, irradiation is terminated. Consequently, there is provided a charged-particle beam irradiation method making it possible to irradiate a charged-particle beam by an accurate dose to an accurate position without the necessity of moving an irradiated subject.

Moreover, according to the present invention, in the charged-particle beam irradiation method, at the fourth step, the angle of rotation of the scanning field generating means is retained at a certain value, the intensity of a field generated by the scanning field generator and the energy of a charged-particle beam are modified in given order, and thus the first to third steps are repeated. Consequently, there is provided a charged-particle beam irradiation method effective in shortening the total time required for irradiation by reducing the frequency of adjusting the angle of rotation that varies slowly.

Moreover, according to the present invention, a charged-particle beam irradiation method, in which a scanning field generating means for generating a scanning field composed of a pair of fields effective in bending a charged-particle beam by the same angle in mutually opposite directions is used to sweep the charged-particle beam along a straight line on a plane perpendicular to the axis of incidence of the charged-particle beam for the purpose of scan, and rotated with the axis of incidence as a center in order to irradiate the charged-particle beam to a radiation area, comprises: a first step of setting the energy of a charged-particle beam to be irradiated according to a coordinate of a position indicating a depth to which a beam is irradiated, $Z_i$ ($i=1$ that is an initial value), specified in a group of coordinates [($z_i$, $\theta_{ij}$), $i=1, 2, \ldots, m$, $j=1, 2, \ldots, n$] defining a radiation area; a second step of specifying the angle of rotation of the scanning field generating means in $\theta_{ij}$ ($j=1$ that is an initial value) and specifying a set, which defines a scan pattern that is a characteristic curve relative to time, in $I_{ij}(t)$; a third step of irradiating a charged-particle beam according to the setting and specification, driving the scanning field generating means according to the scan pattern that is the characteristic curve relative to time defined by $I_{ij}(t)$, and thus shifting the spot of the charged-particle beam so as to achieve a given number of scans; a fourth step of judging in parallel with the third step whether or not a coordinate of a position to which a charged-particle beam is irradiated is consistent with a coordinate of a pre-set position; a fifth step of, when the given number of scans has been carried out or when the coordinate of the position to which a charged-particle beam is irradiated is inconsistent with the coordinate of the pre-set position, stopping the charged-particle beam; and a sixth step at which when a charged-particle beam is stopped, it is judged whether or not irradiation to the whole radiation area is completed, at which if the irradiation is completed, irradiation is terminated, at which if the irradiation is not completed, it is judged whether or not the coordinate of the position indicating a depth to which a beam is irradiated, $Z_i$, should be changed to the next value, at which if the coordinate should not be changed, j is incremented by one, and control is returned to the second step in order to repeat the second to fifth steps, and at which if the coordinate should be changed, i is incremented by one, j is reset to the initial value 1, and control is returned to the first step in order to repeat the first to fifth steps. Consequently, there is provided a charged-particle beam irradiation method making it possible to irradiate a charged-particle beam by an accurate dose to an accurate position without the necessity of moving an irradiated subject.

Moreover, according to the present invention, in the charged-particle beam irradiation method, the scanning field generating means shifts a beam spot along a radius alone of a radiation area during one beam spill for the purpose of scan, and $I_{ij}(t) \sqrt{t}$ is adopted as $I_{ij}(t)$ defining the scan pattern that is the characteristic curve relative to time. Consequently, there is provided a charged-particle beam irradiation method enabling more uniform irradiation.

What is claimed is:

1. A charged-particle beam irradiation apparatus, comprising:
   a scanning field generator for generating a scanning field composed of a pair of fields effective in bending a charged-particle beam by a same angle in mutually opposite directions; and
   a rotator for rotating the scanning field generator with an axis of incidence of the charged-particle beam as a center.

2. The charged-particle beam irradiation apparatus according to claim 1, wherein said scanning field generator generates magnetic fields.

3. The charged-particle beam irradiation apparatus according to claim 1, wherein said scanning field generator generates electric fields.

4. A charged-particle beam rotary irradiation system, comprising:
   a deflector for deflecting a charged-particle beam so that the charged-particle beam is perpendicular to a radiation plane to be radiated;
   a charged-particle beam irradiation apparatus that includes a scanning field generator, located downstream of said deflector, for generating a scanning field composed of a pair of fields effective in bending a charged-particle beam by a same angle in mutually opposite directions, and a rotator for rotating said scanning field generator with an axis of incidence of the charged-particle beam as a center, and that sweeps the charged-particle beam deflected by said deflector for the purpose of scan;
   a charged-particle beam energy interposed between said charged-particle beam irradiation apparatus and an irradiated subject; and
   a rotary motion device for rotating at least said deflector and charged particle beam irradiation apparatus in one united body.

5. The charged-particle beam rotary irradiation system according to claim 4, wherein said charged-particle beam falls on said deflector from the direction of the axis of rotation of said rotary motion device, and said deflector includes three deflective electromagnets for deflecting an incident charged-particle beam three times by 90° with respect to a direction parallel to a radiation plane so that the charged-particle beam be perpendicular to the radiation plane, and said irradiated subject is positioned on the axis of rotation of said rotary motion device.

6. The charged-particle beam rotary irradiation system according to claim 5, wherein said deflective electromagnets of said deflector are realized with superconducting electromagnets.

7. A charged-particle beam irradiation system, comprising:
   a charged-particle beam irradiation apparatus that includes a scanning field generator for generating a scanning field composed of a pair of fields effective in bending a charged-particle beam by a same angle in mutually opposite directions, and a rotator for rotating said scanning field generator with an axis of incidence of the charged-particle beam as a center, and that sweeps the charged-particle beam for the purpose of scan;

a charged-particle beam energy adjuster, interposed between said charged-particle beam irradiation apparatus and an irradiated subject, for adjusting energy of a charged-particle beam;

a dose/position measuring device, interposed between said charged-particle beam irradiation apparatus and irradiated subject, for monitoring a dose and position of an irradiated charged-particle beam;

a beam stopper for stopping a charged-particle beam;

a controller, for controlling scanning based on one of a number of deposited particles of the charged-particle beam and a number of scanning being carried out.

8. The charged-particle beam irradiation system according to claim 7, wherein said controller includes:

a first means for setting the angle of rotation and field intensity concerning said scanning field generator, and the energy of a charged-particle beam according to a group of coordinates [Pi : i=1, 2, ..., n] (i=1 that is an initial value) defining a radiation area;

a second means for irradiating a charged-particle beam according to the setting;

a third means for, when a number of deposited particles of a charged-particle beam becomes equal to or larger than a pre-set number of particles or when a coordinate of a position to which a charged-particle beam is irradiated is inconsistent with a coordinate of a pre-set position, stopping the charged-particle beam; and a fourth means that when a charged-particle beam is stopped, judges whether or not irradiation to the whole radiation area is completed, that if the irradiation is not completed, increments i by one, modifies the angle of rotation and field intensity concerning said scanning field generator, and the energy of a charged-particle beam in given order, and thus actuates said first to third means repeatedly, and that if the irradiation is completed, terminates irradiation.

9. The charged-particle beam irradiation system according to claim 8, wherein said fourth means retains the angle of rotation of said scanning field generator at a certain value, modifies the intensity of a field generated by said scanning field generator and the energy of a charged-particle beam in given order, and thus actuates said first to third means repeatedly.

10. The charged-particle beam irradiation system according to claim 7, wherein said controller includes:

a first means for setting the energy of a charged-particle beam to be irradiated according to a coordinate of a position indicating a depth to which a beam is irradiated, $Z_i$ (i=1 that is an initial value), specified in a group of coordinates [($Z_i$, $\theta_{ij}$), i=1, 2, ..., m, j=1, 2, ..., n] defining a radiation area;

a second means for specifying the angle of rotation of said scanning field generator in $\theta_{ij}$ (j=1 that is an initial value) and specifying a set defining a scan pattern that is a characteristic curve relative to time in $I_{ij}(t)$;

a third means for irradiating a charged-particle beam according to the setting and specification, driving said scanning field generator according to the scan pattern that is the characteristic curve relative to time defined by $I_{ij}(t)$, and thus sweeping a charged-particle beam so as to achieve a given number of scans;

a fourth means for judging in parallel with the scans achieved by said third means whether or not a coordinate of a position to which a charged-particle beam is irradiated is consistent with a coordinate of a pre-set position;

a fifth means for, when the given number of scans have been carried out or when the coordinate of the position to which a charged-particle beam is irradiated is inconsistent with the coordinate of the pre-set position, stopping the charged-particle beam; and a sixth means that when a charged-particle beam is stopped, judges whether or not irradiation to the whole radiation area is completed, that if the irradiation is completed, terminates irradiation, that if the irradiation is not completed, judges whether or not the coordinate of the position indicating a depth to which a beam is irradiated, $Z_i$, should be changed to the next value, that if the coordinate is not changed, increments j by one, and actuates the second to fifth means repeatedly, that if the coordinate is changed, increments i by one, resets j to the initial value 1, and actuates the first to fifth means repeatedly.

11. The charged-particle beam irradiation system according to claim 10, wherein $I_{ij}(t) \propto \sqrt{t}$ is adopted as $I_{ij}(t)$ defining the scan pattern that is the characteristic curve relative to time to be followed by said scanning field generator.

* * * * *